United States Patent [19]

Sheehan et al.

[11] 4,294,249
[45] Oct. 13, 1981

[54] SWAGE-MOLDED INJECTION SITE

[75] Inventors: Neil J. Sheehan, Berkeley; Melvin H. Norman, Oakland, both of Calif.

[73] Assignee: Cutter Laboratories, Inc., Berkeley, Calif.

[21] Appl. No.: 85,841

[22] Filed: Oct. 18, 1979

[51] Int. Cl.³ .............................................. A61M 5/00
[52] U.S. Cl. .............................. 128/214 G; 128/214.2; 215/247; 215/355
[58] Field of Search ........... 128/214 R, 214 G, 214 C, 128/214.2, 247; 215/232, 247, 274, 355

[56] References Cited

U.S. PATENT DOCUMENTS

| | | | |
|---|---|---|---|
| 3,057,350 | 10/1962 | Cowley | 128/214 G |
| 3,447,570 | 6/1969 | Collens | 128/214 G X |
| 3,776,229 | 12/1973 | McPhee | 128/214 C |
| 3,900,028 | 8/1975 | McPhee | 128/272 |
| 4,133,441 | 1/1979 | Mittleman et al. | 215/320 X |
| 4,219,912 | 9/1980 | Adams | 128/214 G |

*Primary Examiner*—Stephen C. Pellegrino
*Attorney, Agent, or Firm*—Theodore J. Leitereg; Robert E. Allen; Bertram Bradley

[57] ABSTRACT

An injection site is disclosed comprising a self-sealing, puncturable member of resilient material and a housing wherein the puncturable member is compressibly confined by a swage-molded edge on the top of the housing. The injection site may be attached to an injection-receiving receptacle such as a medicament injection device as used in an assembly for intravenous administration.

7 Claims, 10 Drawing Figures

SWAGE-MOLDED INJECTION SITE

BACKGROUND OF THE INVENTION

1. Field of the Invention

This invention relates to and has among its objects the provision of novel injection sites and methods for making them. In particular, one of the objects of the invention is the provision of improved injection sites for medicament injection devices in assemblies used in the administration of parenteral fluids. Further objects of the invention will be evident from the following description.

2. Description of the Prior Art

Customarily, in hospitals supplementary medicaments are administered via hypodermic syringe through resealable, puncturable closures on devices attached to intravenous administration sets which are delivering parenteral solutions or the like to patients. Typical of such devices are those disclosed in U.S. Pat. Nos. 3,332,418 and 3,776,229.

Sterile parenteral solutions are frequently supplied to medical institutions in sterile receptacles. Part of the receptacle is filled with parenteral solution, the remainder is filled with air to allow supplementary medicaments to be added to the sealed containers prior to administration of the solutions to patients. Generally, these receptacles include an injection site through which the aforementioned medicaments can be injected by means of a hypodermic syringe. Usually, the syringe needle is forced through a resealable or self-sealing, puncturable member formed from a resilient material such as rubber. The puncturable member or closure is thus one part of the injection site.

Usually, the puncturable member is secured to the aforementioned receptacle or to the above-mentioned medicament administration device by means of external clamping structures such as metal rings, tape bands, etc. In this way, the ends of the puncturable closure are compressed around that portion of the structure to which the closure is attached which is generally a tubular member, the combination of the closure attached to a portion of the structure being referred to as the injection site.

A number of disadvantages are found in the employment of external clamping means. First, if the clamps are not adequately tightened, they are susceptible to disengagement from the structure when the inserted syringe needle is removed from the puncturable closure. In addition, even if the puncturable member remains attached to the structure, leakage of the receptacle contents may occur because of the insufficiently tightened clamping means. Another disadvantge is the somewhat unpleasant appearance of an injection site which includes external clamps.

In U.S. Pat. Nos. 3,900,028 and 4,133,441 (hereinafter '028 and '441, respectively) injection sites that avoid external clamps are described. The disadvantage of the '028 injection site is that it comprises three members interacting to secure the puncturable member in the assemblage, which requires a cumbersome procedure. The latter ('441) site is disadvantageous because it requires an elaborate puncturable membrane.

Injection sites in which a puncturable member is confined in a plastic housing are disclosed in U.S. Pat. Nos. 4,076,023 and 4,000,740. The patented devices require two mated pieces of plastic which are cemented together after a puncturable member is placed inside. In this fashion the member becomes compressibly housed in the mated plastic pieces. The disadvantage of the patented devices is found in their production, since two pieces of plastic are required and the pieces must be cemented together.

SUMMARY OF THE INVENTION

The invention described herein obviates the problems encountered in the prior art devices. The improved injection site of the invention comprises a self-sealing, puncturable member of resilient material and a housing wherein the puncturable member is compressibly confined by a swage-molded edge on the top of the housing. In a preferred embodiment of the invention the housing is plastic and the edge is ultrasonically swage-molded. The injection site may be attached to an injection-receiving receptacle by appropriate conduit means.

An advantage of the present device is that the puncturable member is securely and compressibly confined in its housing. Leakage around the member and through the needle entry pathway after needle withdrawal is avoided, and disengagement of the puncturable member from the injection site is obviated.

Another advantage of the instant device is its ease of construction. The device can be economically manufactured using mass production techniques. Further, the simplicity of its design affords an attractive assembly. The present device requires a single plastic housing in which a puncturable member is confined.

DESCRIPTION OF THE PREFERRED EMBODIMENTS

Figure 1:
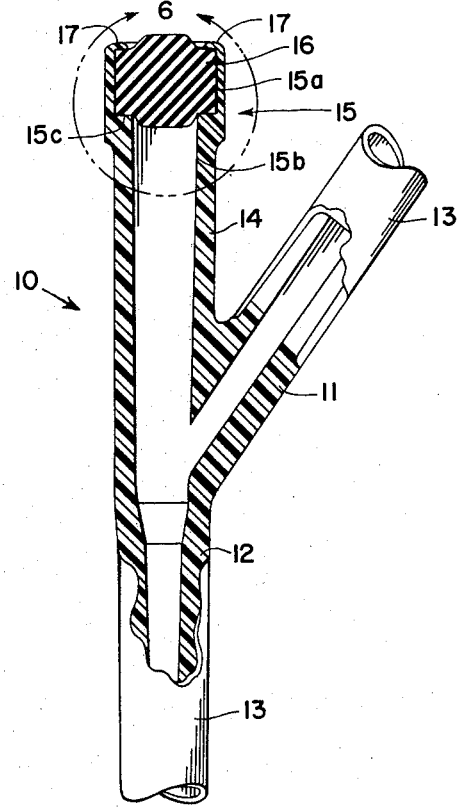
FIG. 1 is a view in partial section of a medicament injection device as used in an assembly for intravenous administration, illustrating an injection site of the invention as part of the device.

Referring to FIG. 1, a medicinal entry or injection device 10 is shown as an integral tubular body member with an inlet 11 and an outlet 12 to which tubing 13 is attached. Tubing 13 is conduit means and connects 10 to a parenteral fluid administration assembly (not shown), intermediate between the fluid supply and the venipuncture needle. Generally, tubing 13 is made of a nontoxic substance conventional in the art and suitable for use with medical liquids. Tubular arm 14, also forming an integral part of device 10, branching from the tubular body member has a housing 15 integrally connected thereto at its end. Compressibly confined in housing 15 is self-sealing, puncturable member 16, which is manufactured from a resilient material such as rubber and the like. The characteristics of member 16 are that it must be puncturable by a needle and it also must be resealable or self-sealing when the needle is withdrawn therefrom so that no leakage can occur through the needle's pathway.

Member 16 is compressibly confined in housing 15 by the cooperation of the top receptor portion 15a of housing 15 and swage-molded edge 17. In the embodiment of FIG. 1 top receptor portion 15a of housing 15 has an inside diameter slightly greater than the diameter of member 16 and greater than the inside diameter of bottom tubular portion 15b of housing 15. The effect of the difference in the inside diameters of 15a and 15b is to produce lip 15c on which the bottom peripheral surface of member 16 rests during its compressive confinement in 15.

Figure 2:
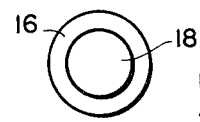
FIG. 2 is a top view of a resealable, puncturable member in accordance with the invention.
Figure 3:
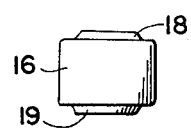
FIG. 3 is a side view of the same puncturable member.
Figure 4:
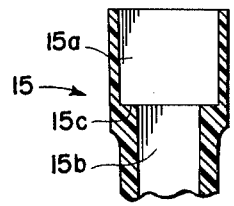
FIG. 4 is a cross-sectional view of a housing in accordance with the invention for the same puncturable member.

Referring to FIGS. 2 and 3, it is desirable that the top surface of member 16 contain a centrally located, raised projection, preferably with a smooth or flat surface. This projection 18 provides a target that is easily ascertained during the use of the injection site of the invention. Thus, the needle may be quickly inserted into member 16 to accurately deliver fluid into outlet 15b (and ultimately to the receptacle to which the injection site is attached, e.g., the injection device 10 of FIG. 1) without disturbing the sidewalls of 15b. In this respect, the diameter of 18 is generally slightly less than the inside diameter of 15b. Additionally, the raised, flat-surfaced projection 18 can be thoroughly cleaned by swabbing with a disinfectant prior to penetration by a needle.

In a preferred embodiment of the invention 16 may contain a centrally located, raised, flat-surfaced projection on both its top and bottom surfaces (18 and 19 in FIG. 3). In automated assembly of the present injection site symmetry of this type is desirable to avoid attitude control since either surface of 16 may be seated in top receptor 15a.

Figure 5:
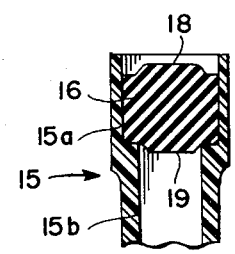
FIG. 5 is a cross-sectional view of the puncturable member of FIG. 3 seated in the housing of FIG. 4.
Figure 6:
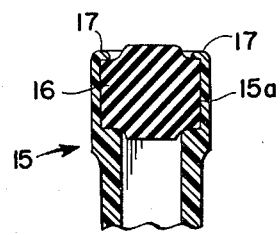
FIG. 6 is a cross-sectional view of an injection site in accordance with the invention and also a portion of the top of the device of FIG. 1.
Figure 7:
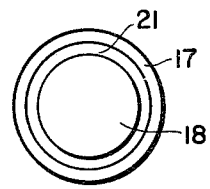
FIG. 7 is a top view of the injection site of FIG. 6.

As mentioned above, 16 is compressibly confined in 15 by means of swage-molded edge 17. FIG. 5 illustrates member 16 seated in 15 prior to swage-molding. Edge 17 may be formed by application of ultrasonic energy employing an instrument (20) such as that shown in FIG. 8. In practice, 20 is designed to apply ultrasonic energy to the top edge of receptor 15a, to render it pliable and deform it and to produce swage-molded edge 17 (FIGS. 6 and 7). Thus, the top edge of 15a must project upwardly a sufficient amount above the peripheral edge of the top surface of 16 so that edge 17, when formed, adequately confines 16 in 15. It is desirable, howevr, that edge 17 not overlap with projection 18. The design of preference is illustrated in FIG. 7 wherein depression 21 separates edge 17 and projection 18, which is outlined as a result to further accentuate it as a target site for an injection needle.

Figure 8:
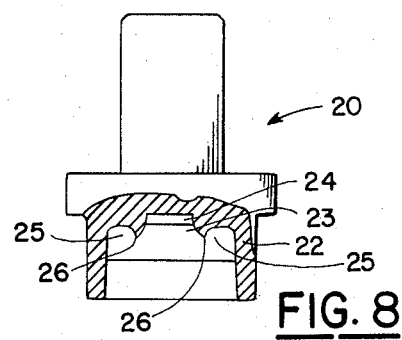
FIG. 8 is a partial sectional view of an ultrasonic tool for making the swage-molded edge in accordance with the invention.

Instrument 20 is conventional in the art but includes a tip portion specially designed for producing swage-molded edge 17. Referring to FIG. 8, the tip of 20 comprises housing 22 having an inside diameter which allows 15 (containing 16) to be slidably received therein. The inside top portion of 22 has the general pattern that will produce the design of the swage-molded edge depicted in FIGS. 6 and 7. Hollow, central portion 23 conforms to the dimensions of projection 18, and 24 is an air space above 23 which is unoccupied during the swage-molding operation. The inside top portion of 22 also includes depression 25. The top edge of 15a softens under the application of ultrasonic energy and is urged downwardly under pressure by 25 until edge 17 is firmly seated against the top peripheral surface of member 16 which becomes sealably compressed in housing 15. Projection 26 shapes edge 17 and yields depression 21 as depicted in FIGS. 6 and 7. Preferably, projection 18 extends above the swage molded top edge of 15.

It should be obvious that housing 15 must be manufactured from an ultrasonically-moldable substance, preferably a medically acceptable plastic such as styrene-acrylonitrile, acrylonitrile-butadiene-styrene, and the like. Conventional ultrasonic assembly equipment may be employed using the modified instrument (20) as described above. Typically, conventional ultrasonic welding systems operate at 20,000 kilohertz. Housing 15 containing member 16 is placed inside housing 22 of 20 and ultrasonic energy is applied for a period (weld time) and under a downward force (pressure) sufficient to swage-mold edge 17. It should be noted that a stop is generally employed on the ultra-sonic assembly equipment to obtain the proper contact of 20 with 15 so that the aforementioned configuration of the top of the swage-molded product is realized. Then, energy is discontinued and the swage-molded injection site is left within the device for a period of time (dwell time) to allow the housing to rigidify and to prevent compressibly confined member 16 from easing edge 17 in a non-compressing direction. The particular amount of energy, weld time, pressure, and dwell time depend upon the type and gauge or thickness of the plastic employed and are easily ascertained for a particular material and gauge by pilot trials in accordance with the teaching of this disclosure.

In a typical instance where 15 is formed of styrene acrylonitrile approximately 0.5 mm thick, the following conditions were employed:

Branson Model 8400 (Branson Sonic Power Co., Danbury, Connecticut) ultrasonic assembly system, 20,000 kilohertz, weld time=0.4 seconds, dwell time=2 seconds, pressure=10 psig.

In the above description the use of ultrasonic energy to mold edge 17 has been emphasized. Ultrasonic energy is preferred for purposes of the invention because of its celerity and because under proper conditions it does not cause any degradation of the plastic housing or rubber member. It should be pointed out, however, that any energy capable of molding edge 17 without damaging the housing or puncturable member may be used in a practice of the invention.

Figure 9:
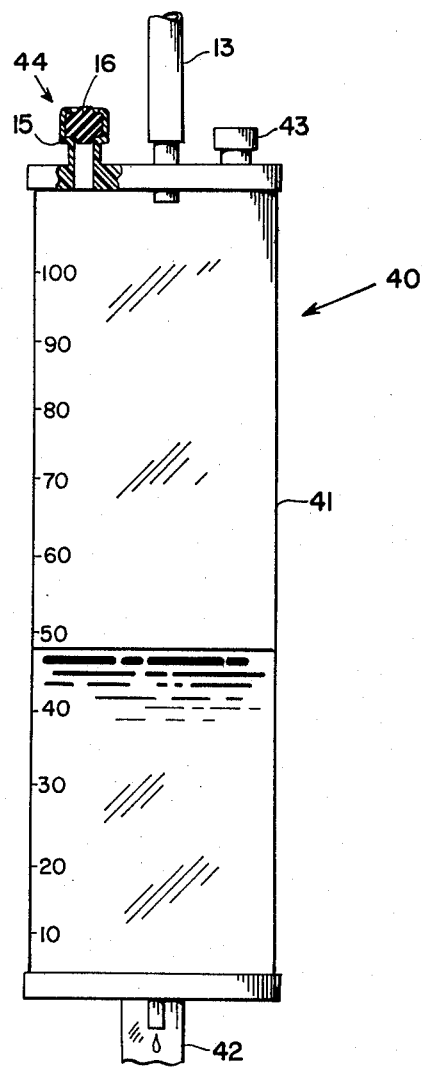
FIG. 9 is a view of a volumetric delivery device as used in an intravenous administration assembly, illustrating another application of the injection site of this invention on an injection port.
Figure 9:
Figure 10:
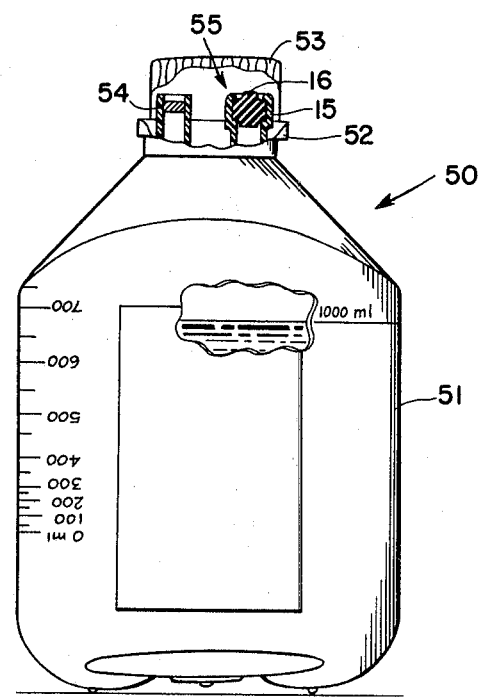
FIG. 10 is a view of a medical liquid container, illustrating another application of the present injection site.

The injection site of the invention has broad utility and may be used in conjunction with all types of injection ports on all kinds of injection-receiving receptacles. FIGS. 9 and 10 depict, by way of illustration and not limitation, two other apparatus on which the present injection site may be employed.

FIG. 9 shows a volumetric fluid delivery device 40 frequently incorporated in intravenous solution administration assemblies. It is generally characterized by a closed transparent rigid column 41 with a drip chamber 42 at the bottom, a filtered airway 43 and a medical entry port 44. As can be seen the injection port includes an injection site of the invention.

FIG. 10 depicts a medical liquid container 50 with bottle 51 and neck 52. Cap 53 on neck 52 covers rigid tube 54 which is structured for connection with an administration set through which liquid is dispensed to a patient. Neck 52 further includes injection port 55 comprising an injection site in accordance with the invention.

The injection site of the invention may also be used in the chemical arts where injection of reactant materials into reaction chambers through injection ports must be employed to avoid contact with air or moisture. Other uses of the present injection site will be obvious to those in the art and are within the scope of this disclosure.

Having thus described the invention, what is claimed is:

1. An injection site, comprising in combination:
  a. a self-sealing, puncturable member of resilient material, said puncturable member being a generally cylindrical body having a top surface on which is centrally located a flat, smooth surfaced raised projection, and
  b. a generally tubular, plastic housing wherein said puncturable member is compressibly confined, said housing having a top receptor portion whose inside diameter is greater than the inside diameter of the remaining portion of the housing so as to provide a ledge on which said puncturable member rests, the top receptor portion having a swage-molded top edge which extends over at least a portion of the top surface of said puncturable member, said swagemolded top edge being below the flat surface of said raised projection.

2. The injection site of claim 1 wherein the swage-molded top edge is an ultrasonically swage-molded top edge.

3. The injection site of claim 1 wherein the bottom surface of said puncturable member has a centrally located, raised projection.

4. The injection site of claim 1 which further includes means for attaching said housing to an injection receiving receptacle.

5. The injection site of claim 1 wherein said site seals an opening on a medicament injection port in an assembly for parenteral fluid administration.

6. The injection site of claim 5 wherein said site seals the opening of a port in a medicament injection device having three interconnecting tubular arms, two of said arms providing inlet and outlet means for communication with conduit means in said assembly, the outer end of said third arm providing the opening of said injection port.

7. The injection site of claim 5 wherein said assembly includes a volumetric fluid delivery device having said injection port located on its top surface.

* * * * *